US011781112B2

(12) United States Patent
Robinson

(10) Patent No.: US 11,781,112 B2
(45) Date of Patent: Oct. 10, 2023

(54) METHOD OF GENERATING ANTIGEN-SPECIFIC IMMUNOLOGICAL MEMORY IN A SUBJECT THAT REJECTS CLASSICAL VACCINES

(71) Applicant: Kareem Thomas Robinson, Baltimore, MD (US)

(72) Inventor: Kareem Thomas Robinson, Baltimore, MD (US)

( * ) Notice: Subject to any disclaimer, the term of this patent is extended or adjusted under 35 U.S.C. 154(b) by 0 days.

(21) Appl. No.: 15/449,953

(22) Filed: Mar. 4, 2017

(65) Prior Publication Data

US 2017/0252426 A1 Sep. 7, 2017

Related U.S. Application Data

(60) Provisional application No. 62/304,234, filed on Mar. 6, 2016.

(51) Int. Cl.

| | |
|---|---|
| ***A61K 39/145*** | (2006.01) |
| ***C12N 5/0781*** | (2010.01) |
| ***C07K 16/10*** | (2006.01) |
| ***A61K 39/00*** | (2006.01) |

(52) U.S. Cl.

CPC ............ *C12N 5/0635* (2013.01); *A61K 39/00* (2013.01); *A61K 2039/545* (2013.01); *Y02A 50/30* (2018.01)

(58) Field of Classification Search

None

See application file for complete search history.

(56) References Cited

U.S. PATENT DOCUMENTS

| | | | | |
|---|---|---|---|---|
| 8,247,228 | B2 * | 8/2012 | Ettinger | A61K 35/17 435/325 |
| 9,273,118 | B2 * | 3/2016 | Beaumont | C07K 16/00 |
| 9,701,736 | B2 | 7/2017 | Jiang et al. | |
| 9,708,583 | B2 * | 7/2017 | Mallone | C12N 5/0636 |
| 9,709,567 | B2 | 7/2017 | Jayaraman et al. | |
| 9,718,874 | B2 | 8/2017 | Spits et al. | |
| 9,719,141 | B2 | 8/2017 | Agnello | |
| 2002/0006409 | A1 * | 1/2002 | Wood | A61P 35/00 424/184.1 |
| 2012/0251502 | A1 | 10/2012 | Towner et al. | |

OTHER PUBLICATIONS

Johansson et al. (PNAS, 1987, vol. 84, p. 6869-6873).*
Joseph et al. (Virology. 2010; 84(13): 6645-6653).*
Cervenka et al. (Journal of Immunology, 1999, p. 5535-5543).*
Schumann et al. (PNAS, 2015, vol. 112, p. 10437-10442).*
Yasugi et al. (Gen Bank Accession No. AB729125.1, 2013).*
Yasugi et al. (PLOS, 2013, vol. 9, p. 1-12).*
Louis J. McHeyzer-William, Antigen-specific B cell Memory, Journal of Experimental Medicine,Apr. 3, 2000; 191(7): 1149-1166.
William Hoffman,B Cells, Antibodies, and More,Clin J Am Soc Nephrol. Jan. 7, 2016; 11(1): 137-154.Dec. 23, 2015.
Karin Klenovsek, Protection from CMV infection in immunodeficient hosts by adoptive transfer of memory B cells, bloodjournal.
Marie Anson, Regulation ana Maintenance of an Adoptive T-Cell Dependent Memory B Cell Pool, PLOS ONE, Nov. 23, 2016.
Thomas Dorner, Selecting B cells and plasma cells to memory, J Exp Med. Feb. 21, 2005; 201(4): 497-499. doi: 10.1084/jem.20050218.
Griselda Zuccarino-Catania, Adoptive Transfer of Memory B Cells, Bio Protoc. Aug. 20, 2015; 5(16): e1563.
Jason K. Whitmire, Tentative T Cells: Memory Cells are Quick to Respond but Slow to Divide, PLoS Pathog. Apr. 2008; 4(4): e1000041.

* cited by examiner

*Primary Examiner* — Agnieszka Boesen

(57) ABSTRACT

The disclosed method provides a novel approach of generating antigen-specific Immunological Memory in a subject which consists primarily of extracting and purifying monocytes, naive T and B lymphocytes from a subject and educating said lymphocytes against a pathogen in vitro until a population of antigen-specific memory lymphocytes are generated with a memory against an infectious agent. Said memory lymphocytes are administered to a subject in a solution which consist primarily of blood plasma derived from said subject. In embodiments, one will see a vaccine approach wherein said vaccine excludes the inoculation of attenuated or killed whole pathogens, where inoculation of said vaccine does not illicit an immune response upon inoculation, and where said vaccine excludes chemicals such as thimerosal, formaldehyde, and aluminum which is all shunned by anti-vaccinators.

3 Claims, 4 Drawing Sheets

Specification includes a Sequence Listing.

Purify either Measles, Mumps, Rubella, Influenza, Polio, Rabies, Small Pox, Hepatitis A, B, and/or C, Zika, Yellow Fever, Japanese Encephalitis, Dengue Fever, HPV, and/or Ebola antigen-specific adaptive immune naive T cells, antigen-specific adaptive immune naive B cells, and monocytes from whole blood and place in cultures. Expand cultures in vitro and convert monocytes into dendritic cells and/or macrophages.

Monocyte derived macrophages and dendritic cells.

Monocyte derived macrophages and dendritic cells.

Anti-Measles Lymphocytes

Anti-Hepatitis C Lymphocytes

Anti-Influenza Lymphocytes

Anti-Zika Lymphocytes

Anti-Ebola Lymphocytes

Anti-Rabies Lymphocytes

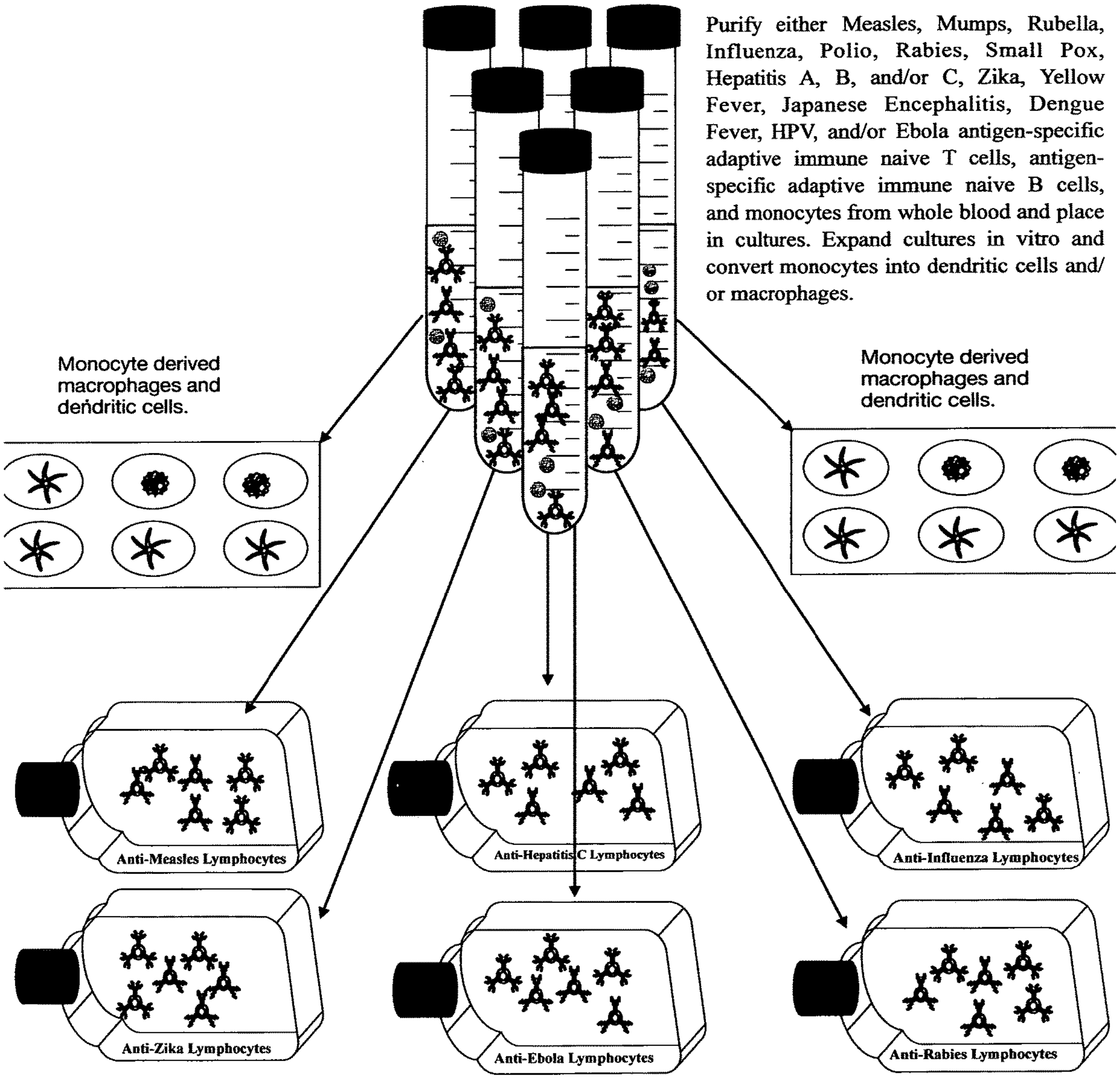

Fig. 1

Pulse microbial antigens with professional antigen-presenting cells (APCs). Introduce antigen-specific lymphocytes with pulsed professional APCs until a population of antigen-specific memory lymphocytes are generated.

Collect antigen-specific memory lymphocytes and place in culture.

Test antibodies which were generated in vitro from B lymphocytes for an affinity against its targeted antigen from each culture.

Genetically modify cultures of anti-Influenza memory B cells with genes for anti-Influenza broadly neutralizing antibodies. After modification, prepare for administration.

Knock-in genes for anti-Influenza broadly neutralizing antibodies.

Anti-Influenza memory B cells

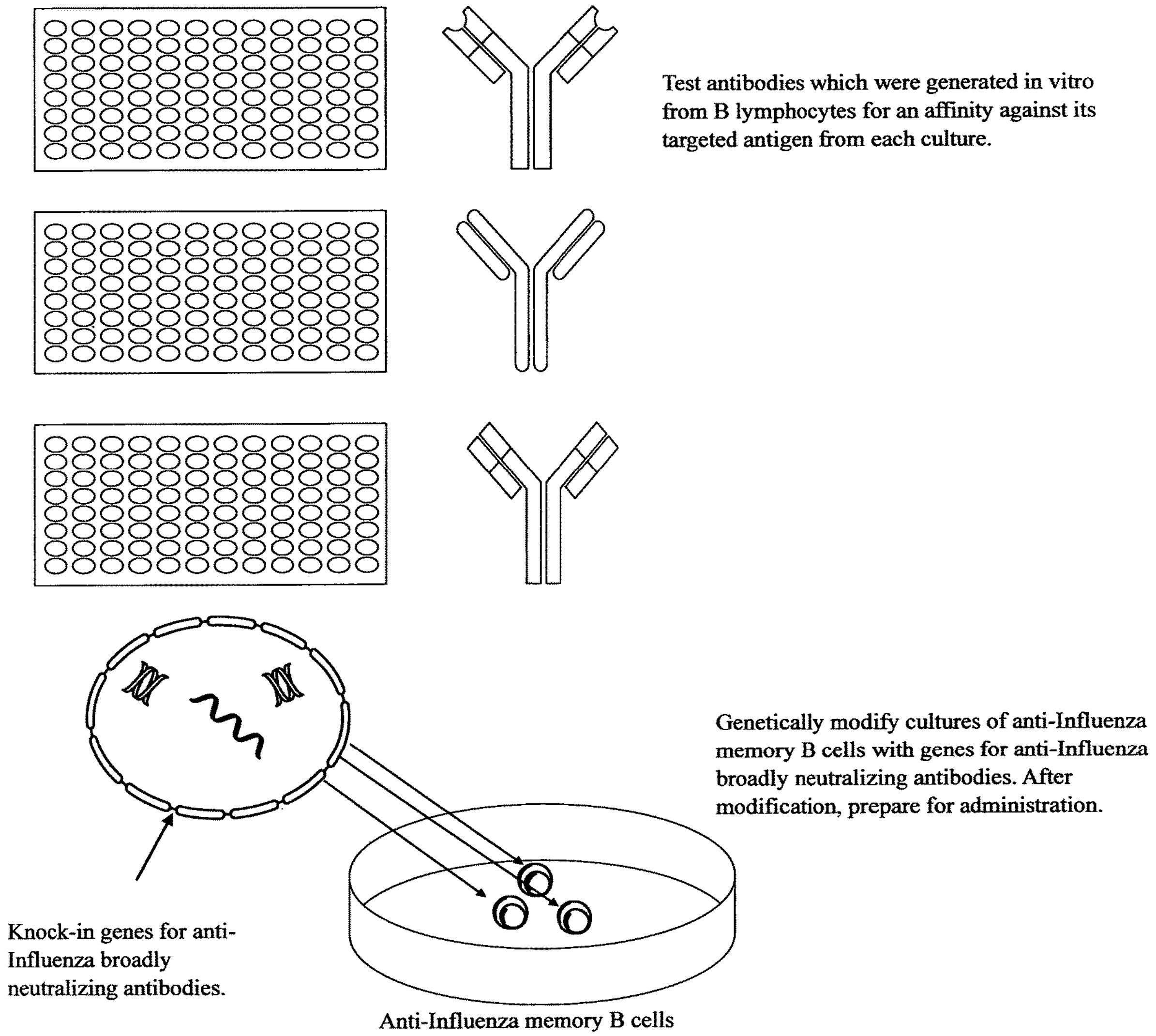

Fig. 3

SEQUENCE LISTING

<160> NUMBER OF SEQ ID NOS: 8

<210> SEQ ID NO 1
<211> LENGTH: 390
<212> TYPE: DNA
<213> ORGANISM: Artificial Sequence
<220> FEATURE:
<223> OTHER INFORMATION: cDNA/IgG-VL-10C4 anti-Influenza-B immunoglobulin lambda chain variable region

<400> SEQUENCE: 1
atggcctggg ctcttctgct cctcaccctc ctcactcact gtgcagggtc ctgggcccag 60
tctgtgctga ctcagccacc ctcagcgtct gggacccccg ggcagagggt ctccatctct 120
tgttctggag gcagctccaa catcggaagt aatactgtaa actggtacca gcagctccca 180
ggaacggccc ccagactcct catctatagc aataatcagc ggcccttagg ggtccctgac 240
cgattctctg agtccaagtc tggcacctca gcctccctgg ccatcagtgg gctccggtct 300
gaggatgagg ctgattatta ctgtgctgca tgggatgaca gcctgaatgg ttgggtgttc 360
ggcggaggga ccaggctgac cgtcctaggt 390

<210> SEQ ID NO 2
<211> LENGTH: 456
<212> TYPE: DNA
<213> ORGANISM: Artificial Sequence
<220> FEATURE:
<223> OTHER INFORMATION: cDNA/IgG-VH-10C4 anti-Influenza immunoglobulin heavy chain variable region

<400> SEQUENCE: 2
atggagtttg ggctgagctg gctttttctt gtggctattt taaaaggtgt ccagtgtgag 60
gtgcagctgt tggagtctgg gggaggcttg gtccagccgg gggggtccct gagactctcc 120
tgtgcagcct ctggattcac ctttagcaac tatgccatga gctgggtccg ccaggctcca 180
gggaaggggc tggagtgggt ctcagctatt agtggtggtg gtgattggac atactacgca 240
gactccgtga agggccgatt ctccatctcc agcgacaatt ccaagaacac gctgtatctg 300
caaatgaaca gcctgagagc cgaggacacg gccgtatatt actgtgcgaa agatgtcacg 360
tatttgtatg acagtagtgg ttattactac gggggagccg accgcgatta ttactttgac 420
tactggggcc agggaaccct ggtcaccgtc tcctca 456

<210> SEQ ID NO 3
<211> LENGTH: 387
<212> TYPE: DNA
<213> ORGANISM: Artificial Sequence
<220> FEATURE:
<223> OTHER INFORMATION: cDNA/IgG-VL-5A7 anti-Influenza-B immunoglobulin lambda chain variable region -continued

<400> SEQUENCE: 3
atggcctggg tctcattcta cctcaccctc ctcactcact gtgcagggtc ctgggcccag 60
tctgtgctga ctcagccacc ctcagcgtct gggacccccg ggcagagggt caccatctct 120
tgttctggaa gcagctccaa catcggaagt aatgatgtct attggtacca gaacctccca 180
ggaacggccc ccaaactcct catctataat aataatcaac ggccctcagg ggtccctgac 240
cgattctctg gctccaagtc tggcacctca gcctccctgg ccatcagtgg gctccggtcc 300
gaggatgagg ctgattatta ttgtgcagca tgggatgaca gcctgactgt ctccttcgga 360
actgggacca aggtcaccgt cctaggt 387

<210> SEQ ID NO 4
<211> LENGTH: 423
<212> TYPE: DNA
<213> ORGANISM: Artificial Sequence
<220> FEATURE:
<223> OTHER INFORMATION: cDNA/IgG-VH-5A7 anti-Influenza-B immunoglobulin heavy chain variable region

<400> SEQUENCE: 4
atggagtttg ggctgagctg ggttctcctc gttgctcttt taagaggtgt ccagtgtcag 60
gtgcagctgg tggagtctgg gggagacgtg gtccaacctg ggaggtccct gagactctcc 120
tgcgcagcgt ctggattcac cttcaataac tatggcatgc actgggtccg ccaggctcca 180
ggcaaggggc tggagtgggt ggcagttgtc tggtatgatg gacttattaa atactatgcg 240
gactccgtga agggccgatt caccatctcc agagacaatt cgaaaaacac cctgtatctg 300
caaatgaaca ccctgagagc cgaggacatg ggtgtctatt actgtgcgag agatctacag 360
cctccccatt caccctacgg tatggacgtc tggggccaag ggaccacggt caccgtctcc 420
tca 423

<210> SEQ ID NO 5
<211> LENGTH: 381
<212> TYPE: DNA
<213> ORGANISM: Artificial Sequence
<220> FEATURE:
<223> OTHER INFORMATION: cDNA/IgG-VL-3A2 anti-Influenza-B immunoglobulin kappa chain variable region

<400> SEQUENCE: 5
atggaagccc cagcgcagct tctcttcctc ctgctactct ggctcccaga taccagtgga 60
gaaataggga tgacgcagtc tccagccacc ctgtctgtgt ctccagggga aagagccacc 120
ctcttttgca gggccagtcc gagtattagc gacaacttag cctggtacca gcagaaacct 180
ggccaggctc ccaggctcct cttctatggt gcatccacca gggccactgg tatcccagcc 240
aggttcagcg gcagtgggtc tgggacagag ttcactctca ccatcagcag tgtgcagtct 300
gaagatattg gagtttatta ttgtcagcag tatagtaact ggcctcgtac ttttggccag 360
gggaccaagc tgcagatcaa a 381

<210> SEQ ID NO 6
<211> LENGTH: 441
<212> TYPE: DNA
<213> ORGANISM: Artificial Sequence
<220> FEATURE:
<223> OTHER INFORMATION: cDNA/IgG-VH-3A2 anti-Influenza-B immunoglobulin heavy chain variable region

<400> SEQUENCE: 6

-continued

```
atgaaacacc tgtggttctt cctcctcctg gtggcagctc ccagatgggt cctgtcccag     60

gtgcagctgg tggagtcggg cccaggactg gtgaagcctt ctgagaccct gtccctcacc    120

tgcactgtct ctagtggctc catcagtagt tactactgga gctggatccg gcagcccccc    180

gggaagggac tggagtggat tgggtatgtc tataacagtg ggagtaccag gtacaacccc    240

tccctcaaga gtcgcctcac catgtcagtg gacgcgtcca ggaagcaggt ctccctgaag    300

ttgagctctg tgagtgctgc ggacacggcc gtgtattact gtgcgagagc cccggacgat    360

tactatgata gtgttggtta ttactacgga tgtccgtact tcgactcctg gggccaggga    420

accctggtca ccgtctcctc a                                              441


<210> SEQ ID NO 7
<211> LENGTH: 702
<212> TYPE: DNA
<213> ORGANISM: Artificial Sequence
<220> FEATURE:
<223> OTHER INFORMATION: cDNA/5j8 anti-Influenza-H1N1 HA immunoglobulin
      lambda light chian

<400> SEQUENCE: 7

atggcctggg ctctgctgct tctcggcctc ctctctcact gcacaggctc tgtgacctcc     60

tatgtgctga ctcagccacc ctcggtgtca gtggccccag gagagacggc caggatttcc    120

tgtgggggaa acaacattgg aactaaagtt ctacactggt accagcagac gccaggccag    180

gcccctgtgc tcgtcgtcta tgatgacagc gaccggccct cagggatccc tgagcgattc    240

tctggctcca actctgggaa cacggccacc ctgaccatca gcagggtcga agtcggggat    300

gaggccgact attactgtca ggtgtgggat atcagtactg atcaagcggt attcggcgga    360

gggaccaaac tgaccgtcct aggtcagccc aaggctgccc cctcggtcac tctgttcccg    420

ccctcctctg aggagcttca agccaacaag gccacactgg tgtgtctcat aagtgacttc    480

tacccgggag ccgtgacagt ggcctggaag gcagatagca gccccgtcaa ggcgggagtg    540

gagaccacca caccctccaa acaaagcaac aacaagtacg cggccagcag ctatctgagc    600

ctgacgcctg agcagtggaa gtcccacaga agctacagct gccaggtcac gcatgaaggg    660

agcaccgtgg agaagacagt ggcccctaca gaatgttcat ag                       702


<210> SEQ ID NO 8
<211> LENGTH: 369
<212> TYPE: DNA
<213> ORGANISM: Artificial Sequence
<220> FEATURE:
<223> OTHER INFORMATION: cDNA/5j8 anti-Influenza-H1N1 HA immunoglobulin
      heavy chain variable region

<400> SEQUENCE: 8

gaggtgcagc tggtggagtc tggcccagga ctggtgaagc cttcggacat cctgtccctc     60

acctgcgctg tctctggtta ctccatcagc agtaattact actggggctg gattcggcag    120

cccccaggga aggggctgga gtggattggg agtatctatc atagtgggag cacctactac    180

aagccgtctc tcgagagtcg actcggcata tcagtagaca cgtccaagaa ccaattctcc    240

ctgaagttga gttttgtgtc cgccgcagac acggccgtgt actattgtgc gcgacatgtt    300

aggagtggtt accccgatac tgcatactac tttgacaagt ggggccaggg aaccctggtc    360

accgtctcc                                                            369
```

METHOD OF GENERATING ANTIGEN-SPECIFIC IMMUNOLOGICAL MEMORY IN A SUBJECT THAT REJECTS CLASSICAL VACCINES

CROSS-REFERENCE TO RELATED APPLICATIONS

This application claims the benefit of U.S. provisional patent application Ser. No. 62/304,234, filled 2016 Mar. 6 by the present inventor.

RELATED U.S. PATENT DOCUMENTS

| Application Number | Filing Date | Patent Number | Issue Date |
|---|---|---|---|
| 62/304,234 | Mar. 6, 2016 | | |

REFERENCES CITED [REFERENCED BY]

U.S. Patent Documents

| | | |
|---|---|---|
| 3,133,861 | May 1964 | Schwarz et al. |
| 20120251502 | October 2012 | Towner; Jonathan S. et al. |
| 7,030,228 | April 2006 | Schmitz et al. |
| 9,273,118 | March 2016 | Beaumont et al. |

OTHER REFERENCES

Cell expansion (n.d.). *GE Healthcare Life Sciences*. Retrieved Jan. 4, 2017 from https://promo.gelifesciences-.com/GL/XURI/expansion.html#.WG2KMqOZPUo Harmsen, I. A., Ruiter, R. A. C., Paulussen, T. G. W., Mollema, L., Kok, G., & de Melker, H. E. (2012). Factors That Influence Vaccination Decision-Making by Parents Who Visit an Anthroposophical Child Welfare Center: A Focus Group Study. *Advances in Preventive Medicine,* 2012, 175694. http://doi.org/10.1155/2012/175694

Fenwell. Retrieved Feb. 28, 2017 from: fenwalinc.com/Pages/Alyx.aspx

Mahmood, T., & Yang, P.-C. (2012). Western Blot: Technique, Theory, and Trouble Shooting. *North American Journal of Medical Sciences,* 4(9), 429-434. http://doi.org/10.4103/1947-2714.100998

MMR (Measles, Mumps, & Rubella) VIS (2012, April) *CDC Web Site*. Retrieved from https://www.cdc.gov/vaccines/hcp/vis/vis-statements/mmr.html Origene Technologies Inc. Retrieved Jan. 4, 2017, from: http://origene.com/CRISPR-CAS9/

Origene Technologies Inc. Retrieved Jan. 9, 2017 from: origene.com/search/ProductList.aspxkeyword=variable+region&go.x=0&go.y=0.

Origene Technologies Inc. Retrieved Jan. 9, 2017 from: www.origene.com/orf/?utm_source=Bing&utm_medium=cpc&utm_term=cDNA%2Bclone&utm_content=cDNA%2Bclones&utm_campaign=Top%2BKeywords Patient Centered Medicine 2: Basic Screening Physical Examination. lumen, n.d. Web, 4 Jan. 2017, http://www.meddean.luc.edu/lumen/meded/ipm/Ipm2/BSE_laminated %20card.pdf Rosette Sep: Unique Immunodensity Cell Isolation. (n.d.). *Stem Cell Technologies Inc.* Retrieved Jan. 4, 2016 from: https://www.stemcell.com/products/brands/rosettesep.html#

Tabacchi, G., Costantino, C., Napoli, G., Marchese, V, Cracchiolo, M., Casuccio, A., on behalf of the ESCULAPIO working group. (2016). Determinants of European parents' decision on the vaccination of their children against measles, mumps and rubella: A systematic review and meta-analysis. *Human Vaccines & Immunotherapeutics,* 12(7), 1909-1923. http://doi.org 10.1080/21645515.2016.1151990

World Health Organization, WHO guidelines on drawing blood: best practices in phlebotomy, 2010. Web, 4 Jan. 2017 from: http://apps.who.int/iris/bitstream/10665/44294/1/9789241599221_eng. pdf

TECHNICAL FIELD

The present invention relates to a novel method of generating antigen-specific Immunological Memory in a subject that shuns classical vaccines due to medical. psychological. or superstitious reasons.

BACKGROUND

Certain factions of the public, fear traditional methods of vaccination because of the assumed/rumored harmful chemicals that is associated within its solution. It is claimed, that chemicals such as thimerosal, formaldehyde, and aluminum contain properties that are detrimental to the health of a patient especially a newborn. Because of said fears, pathogens such as measles and whooping cough are starting to appear in the developed world, and herd immunity is now in jeopardy. Current methods of vaccination includes the inoculation of live attenuated or killed whole pathogens directly into a patient. Vaccines such as the MMR utilizes killed whole measles pathogens, see for example, U.S. Pat. No. 3,133,861. The MMR vaccine triggers an immune response which varies between patients. In some patients, the immune response can trigger a reaction which includes swelling, pain at injection site, swelling of glands, seizures, or an allergic reaction. In very rare cases, vaccines such as the MMR can cause deafness, long-term seizures, coma, or lowered consciousness, and permanent brain damage (MMR, 2012, para. 7). Because of this, certain factions of the public refuse vaccinations for themselves or family members and are currently demanding a vaccine which does not trigger an immune response, which excludes attenuated or killed whole pathogens, and which do not contain certain chemicals mentioned earlier. Traditional methods of vaccination which have worked successfully against most pathogens suffer from a number of drawbacks:

(a) Models proposed includes the use of chemicals such as thimerosal, aluminum, and formaldehyde in its vaccine solution. Certain factions of the public fear said chemicals associated within the solution of vaccines and refuse vaccination for themselves or family members from fear of medical complications.

(b) Traditional vaccine regiments causes an immune response in patients which can be either benign or could be the cause of complications such as a fever. In addition, because patients sometimes develop a high immune response after inoculation, they often believe that the vaccine gave them the illness, and feel that it is better to catch the infection naturally.

(c) Current models propose an indirect approach in establishing immunological memory. Indirect because immunogens that were administered to the patient are assumed to have established an effective immunological memory that can elicit neutralizing antibodies upon natural infection with no way of knowing directly.

(d) Immunological memory against viruses such as Ebola must be established in a way that offer patients an adequate amount of memory lymphocytes which have the potential to illicit a high immune response against said pathogen.

SUMMARY

In one embodiment, the invention serves three purposes. (a) It serves as a method of generating antigen specific Immunological Memory against Measles, Mumps, Rubella, Yellow Fever, Small Pox, Varicella Zoster, Polio (Salk), Rabies, Hepatitis A, Hepatitis B, Hepatitis C, HPV (Human Papilloma Virus), Influenza, Japanese Encephalitis, Dengue Fever, whooping cough, etc. which excludes the inoculation of whole killed or attenuated pathogens into a subject, which does not produce an immune response upon inoculation into said subject, and which does not contain chemicals that are shunned by anti-vaccinators such as thimerosal, formaldehyde, or aluminum. (b) It serves as a method to establish Influenza antigen-specific memory lymphocytes with the genetic potential for Influenza broadly neutralizing antibodies in a subject. (c) It serves as a method of vaccination to patients who normally could not vaccinate for medical reasons such as pregnancies, nursing mothers, allergic reactions against traditional vaccines, patients with a history of Guillain-Barré Syndrome (also called GBS), currently suffering from an illnesses such as the flu, under the influence of certain medications, or are being treated for cancer with radiation or drugs.

In embodiments, monocytes, naive T lymphocytes, and naive B lymphocytes are isolated from patient's PBMCs and cultured in vitro.

In embodiments, memory lymphocytes are created from patient's isolated lymphocytes in accord to their targeted pathogen such as a population Influenza antigen-specific memory lymphocytes or a population of Measles antigen-specific memory lymphocytes, etc.

In embodiments, memory lymphocytes are educated for each of the most common infectious strains of pathogens that occur in natural infections. Such as the most common infectious strains of Hepatitis C or the most common infectious strains of Influenza.

In certain embodiments, Influenza antigen-specific memory lymphocytes have genes for broadly neutralizing antibodies against their targeted pathogen knocked in its genome.

In embodiments, memory B lymphocytes are stimulated with pathogens/antigens repeatedly until antibodies of high affinity against its antigenic epitopes are obtained.

In embodiments, memory lymphocytes which were educated against their targeted pathogen in vitro are administered to subject.

In embodiments, memory lymphocytes which were educated in vitro are administered to a subject in a solution which consist primarily of purified blood plasma.

In one aspect, the invention provides memory B lymphocytes which have been educated in vitro to have high antibody affinity against its targeted pathogen.

In another aspect, the invention provides memory CD4 T lymphocytes which have been educated in vitro to orchestrate an immune response against its targeted pathogen.

In yet another aspect, the invention provides CD8 T lymphocytes which have been educated in vitro to recognize pathogenic epitopes presented by infected cells under natural infections.

In certain aspects, the invention provides Influenza antigen-specific memory lymphocytes with the genetic potential for broadly neutralizing antibodies.

BRIEF DESCRIPTION OF THE DRAWINGS

FIGS. 1 & 2 shows an overall description of the process involved in memory lymphocyte generation in vitro.

FIGS. 3 & 4 shows the process of expanding, stimulating, genetically modifying, and preparing antigen-specific memory lymphocytes for administration.

DETAILED DESCRIPTION

Figure 2:
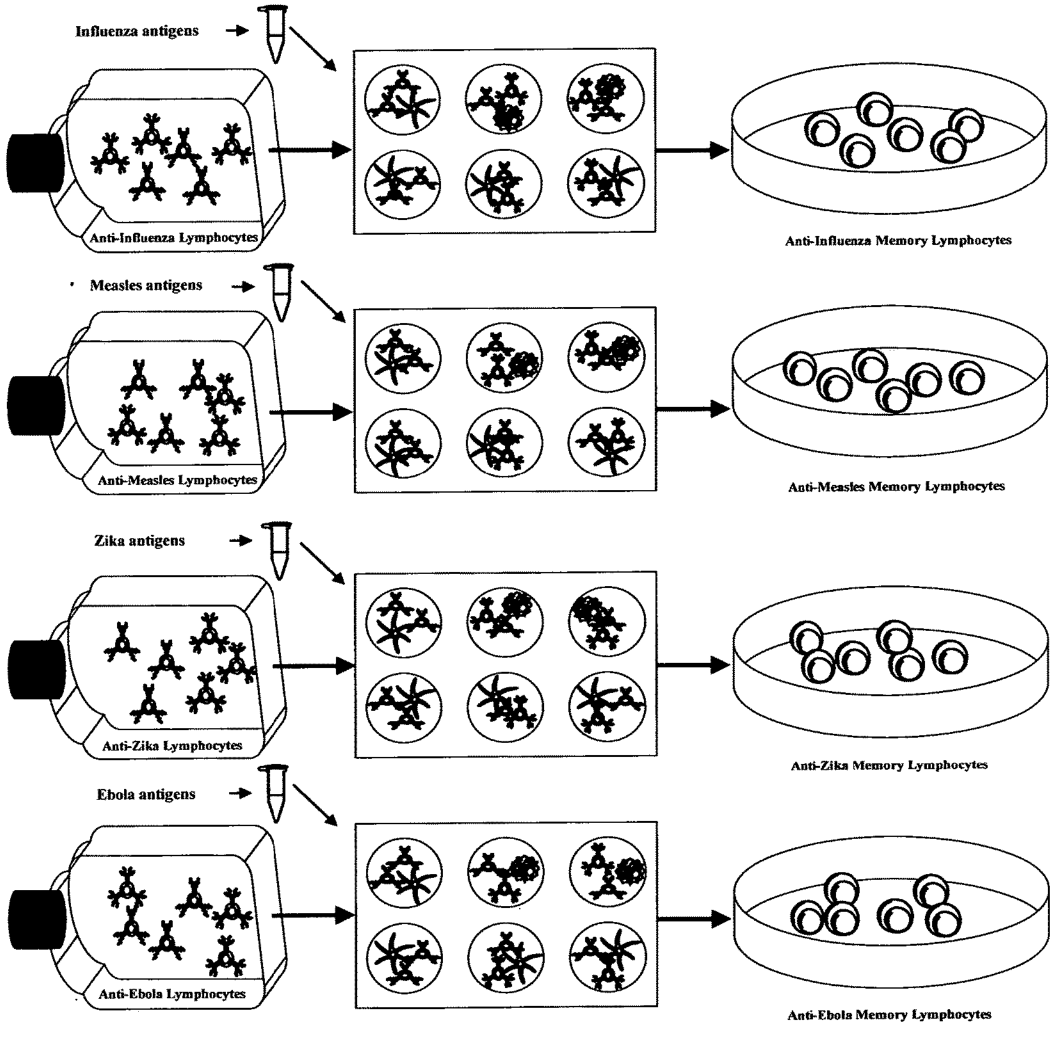

The practice of the present invention employs unless otherwise indicated conventional techniques of molecular biology, microbiology, cell biology, and immunology which are within the skill of the art. Techniques such as cellular isolation, cellular expansion, and genetic modification are provided through commercial kits unless otherwise indicated. Usage of said techniques is explained in the literature/directions provided from vendors.

Definition

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. To facilitate the understanding of this invention, a number of terms are defined below. Terms defined herein have meanings as commonly understood by a person of ordinary skill in the areas relevant to the present invention.

Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

According to the present invention, the general use herein of the term "antigen" refers; to any portion of any antigenic portion of a (peptide), partial protein, and full-length protein wherein the protein is naturally occurring, synthetically made, glycoprotein wherein the glycoprotein contains a carbohydrate portion of the antigen and epitopes of glycoproteins. An antigen can be as small as a single epitope, a single immunogenic domain or larger, and can include multiple epitopes or immunogenic domain, or nucleic acids encoding an antigenic protein.

According to the present invention, antibodies or immunoglobulins are referred to antibodies from mammalian species primarily humans where the antibodies (IgM, IgG, IgD, IgA, IgE) are naturally occurring from B cells.

According to the present invention, a subject is a mammalian species primarily a human.

The term patient refers to the subject receiving treatment which is primarily a human.

As used herein, the term traditional vaccination/vaccine refers to the current methods of inoculating live attenuated, killed whole, pathogens or subunit protein antigens into a patient for the establishment of immunological memory against said pathogen.

As used herein, the term anti-vaccinator refers to a group of like minded individuals who refuse vaccination for themselves and family members due to a fear of medical complications which is believed to occur from vaccination.

As used herein, the term "cytokine" refers to any one of the numerous factors that exert a variety of effects on cells, for example, inducing growth or proliferation. Non-limiting examples of cytokines which may be used alone or in combination in the practice of the present invention include, interleukin-2 (IL-2), interleukin-4 (IL-4), interleukin-6 (Il-6), interleukin-7 (IL-7), interleukin-10 (IL-10), interleukin-15 (IL-15), G-CSF, granulocyte macrophage-colony stimulating factor (GM-CSF), macrophage-colony stimulating factor (M-CSF), b-cell activating factor (BAFF) and CD40 ligand. Cytokines are commercially available from several vendors. It is intended, although not always explicitly stated, that molecules having similar biological activity as wild-type or purified cytokines (e.g., recombinantly produced or muteins thereof) are intended to be used within the spirit and scope of the invention.

The terms "major histocompatibility complex" or "MHC" refers to a complex of genes encoding cell-surface molecules that are required for antigen presentation to T cells and for rapid graft rejection. The proteins encoded by the MHC are known as "MHC molecules" and are classified into Class I and Class II MHC molecules.

The term pathogen refers to any microbial agent which causes human disease primarily those that are attenuated or killed in vaccine regiments.

The term "antigen presenting cells (APCs)" refers to a class of cells capable of presenting one or more antigens in the form of peptide-MHC complex recognizable by specific effector cells of the immune system, and thereby inducing an effective humoral and cellular immune response against the antigen or antigens being presented. APCs can be intact whole cells such as macrophages, B-cells, endothelial cells, activated T-cells, and dendritic cells; or other molecules, naturally occurring or synthetic, such as purified MHC Class I molecules complexed to beta.2-microglobulin. While many types of cells may be capable of presenting antigens on their cell surface for T-cell recognition, only dendritic cells have the capacity to present antigens in an efficient amount to activate naive T-cells for cytotoxic T-lymphocyte (CTL) responses.

The term monocyte refers to a diverse population of similar white blood cells found circulating in peripheral blood. Monocytes have the ability to differentiate into macrophages and dendritic cells.

The term "macrophage" refers to a diverse of population of morphologically similar cells found in a variety of tissues. It is a major APC for the organism. Macrophages can be generated from monocytes in vitro, and are an optional APC for the invention.

The term "dendritic cells (DCs)" refers to a diverse population of morphologically similar cell types found in a variety of lymphoid and non-lymphoid tissues. Dendritic cells constitute the most potent and preferred APCs in the organism. While the dendritic cells can be differentiated from monocytes, they possess distinct phenotypes.

The term "adaptive immune lymphocytes" refers to a diverse population of B cells from the humoral immune system, and T cells from the cellular-mediated immune system. B cells are the humoral immune cells that create antibodies after they have differentiated into plasma cells. T cells from the cell mediated immune system consist of diverse populations primarily of CD4 and CD8 T cells. CD4s or helper T cells help orchestrate the immune response, while CD8 or cytotoxic T cells kill infected cells with active WIC 1 molecules on their plasma membrane.

The term T lymphocytes (T cells) are distinguished from other lymphocytes by the T cell receptor (TCR), which B cells and Natural Killer cells do not express. There are several types of T cells based on their specific function: helper/effector, cytotoxic, memory, regulatory and gamma delta (γδ) T cells. When a pathogen is detected, information is communicated to T cells through antigen presentation. Following activation, naive CD4+ T cells differentiate into one of the several lineages of T helper cells (Th1, Th2, Th9, Th17, or Th22), depending primarily on the antigen, the strength of the TCR signal, and the cytokines present in the surrounding extracellular environment. Differentiation of each T cell subset is associated with the expression of specific transcription factors followed by secretion of a defined array of cytokines that orchestrate a directed response to the antigen.

The term B lymphocytes (B cells) refers to a diverse population of the humoral immune cells. Part of the adaptive immune system, B cells are responsible for generating antibodies to specific antigens, which they bind via B cell receptors (BCR). Activation of B cells occurs via antigen recognition by BCRs and a required co-stimulatory, secondary activation signal provided by either helper T cells or the antigen itself. This results in stimulation of B cell proliferation and the formation of germinal centers where B cells differentiate into plasma cells or memory B cells. Following the primary immune response, a small number of B lymphocytes develop into memory B lymphocytes, which express high-affinity surface immunoglobulins (mainly IgG), survive for a longer period of time, and enable a rapid secondary response.

The term "antigen-specific memory cells" refer to adaptive immune cells that are capable of a secondary immune response to a previously encountered antigen. The antigen-specific memory cells will be obtained in vitro from the invention and will have a memory for the various epitopes contained on the numerous protein antigens of its targeted pathogen. The memory T cells can be either resident, effector, or central memory lymphocytes.

As used herein, the term in vitro refers to a process taking place in culture dishes or test tubes outside of a living organism inside a laboratory or controlled environment.

Overview

Pathogens such as Polio, Small Pox, Measles and Influenza have devastated the developed and developing world until the miracle of vaccination. Vaccines have worked so successfully that the general population have forgotten of the horrors caused by said pathogens."Measles, mumps and rubella (MMR) are serious diseases that can cause significant morbidity and lead to potentially fatal illness, disability and death. Despite the introduction of the trivalent MMR vaccine in the 1970s, measles is still circulating in several regions of Europe, mainly in the form of recurring spatially localized epidemics, with 4,284 cases reported during the recent 12-month period (June 2014-May 2015) in 30 EU/EEA Member States, 77% of which in unvaccinated subjects, and 15.5% in vaccinated with 1 dose" (Tabacchi, G., Costantino, C., Napoli, G., Marchese, V, Cracchiolo, M., Casuccio, A., 2016, para. 2). Patients which go unvaccinated often have a negative disposition against the material and methods involved in said vaccines. One negative disposition is the inoculation of the pathogen which is responsible for the disease. Traditional vaccines come in the form of attenuated or whole killed pathogens which are often genetically modified. The reason for disagreement is the fact that said inoculations often causes an immune response in said patient which varies between individuals and with rare cases can cause an unusual allergic reaction. These reactions, though rare, are making communities question the safety of current vaccination methods and are seeking alternative methods to prevent illnesses. Components associated in MMR vaccines contains chemicals such as thimerosal, aluminum, and formaldehyde, which anti-vaccinators associated with complications such as autism. Even-though current data suggests that said chemicals is not associated with said disorder, any use of said chemicals is often shunned by anti-vaccinators who seek vaccines which are free of said components. "Our findings show that participants did not refuse all vaccinations within the Dutch NIP, but mostly refused the Mumps, Measles, and Rubella (MMR) vaccination. Vaccination decisions are influenced by participants' lifestyle, perception of health, beliefs about childhood diseases, perceptions about the risks of diseases, perceptions about vaccine effectiveness and vaccine components, and trust in institutions" (Harmsen, et al., 2012, para. 1).

The invention offers an alternative method to traditional vaccination methods by excluding the practice of inoculating attenuated or killed whole pathogens directly into patients, but instead inoculating antigen-specific memory lymphocytes which were obtained from a subject and cultured in vitro to have a memory against a particular pathogen. In embodiments, PBMCs (Peripheral Blood Monoclonal Cells) such as monocytes, naive T and naive B cells are obtained from whole blood samples and cultured in. vitro. In. embodiments, PBMCs are derived from the patient or can be derived from a donor, for example, the donor can be a mother and the recipient can be the child of said mother. Said blood samples are purified and expanded in vitro, as well as differentiation of monocytes to Dendritic Cells as shown in FIG. 1. After expansion and differentiation, whole attenuated or whole killed pathogens such as Measles, Mumps, Rubella, Influenza, Polio, Rabies, Small Pox, Hepatitis A, Hepatitis B, Hepatitis C, Zika, Yellow Fever, Dengue Fever, Japanese Encephalitis, HPV (Human Papilloma Virus), etc. can be pulsed with antigen-presenting cells in individual cultures as shown in FIG. 2. In one embodiment, different strains for a particular pathogen can be pulsed with said APCs. For example, APCs can be pulsed with different strains of Influenza or different strains of HCV. After exposure to said pathogens, lymphocytes are further expanded for seven-fourteen days, or until a small amount of antigen-specific memory lymphocytes are obtained. In one embodiment, antigen-specific memory B lymphocytes are re-stimulated with pathogens to increase its antibody affinity against said pathogen. Antigen-specific memory lymphocytes are then prepared for administration to subject or recipient as shown in FIGS. 3 & 4.

In certain embodiments lymphocytes are educated to have a memory against Ebola. Ebola is filovirus which causes hemorrhagic fever. Though rarely encountered, healthcare professionals or military personnel working either with infected patients or traveling to Ebola infested countries need a direct method to insure that their immune system have an adequate amount of immune memory lymphocytes with a memory against Ebola. Ebola antigen-specific memory lymphocytes can be administered to said persons before traveling to said countries or caring for Ebola infected patients.

Figure 4:
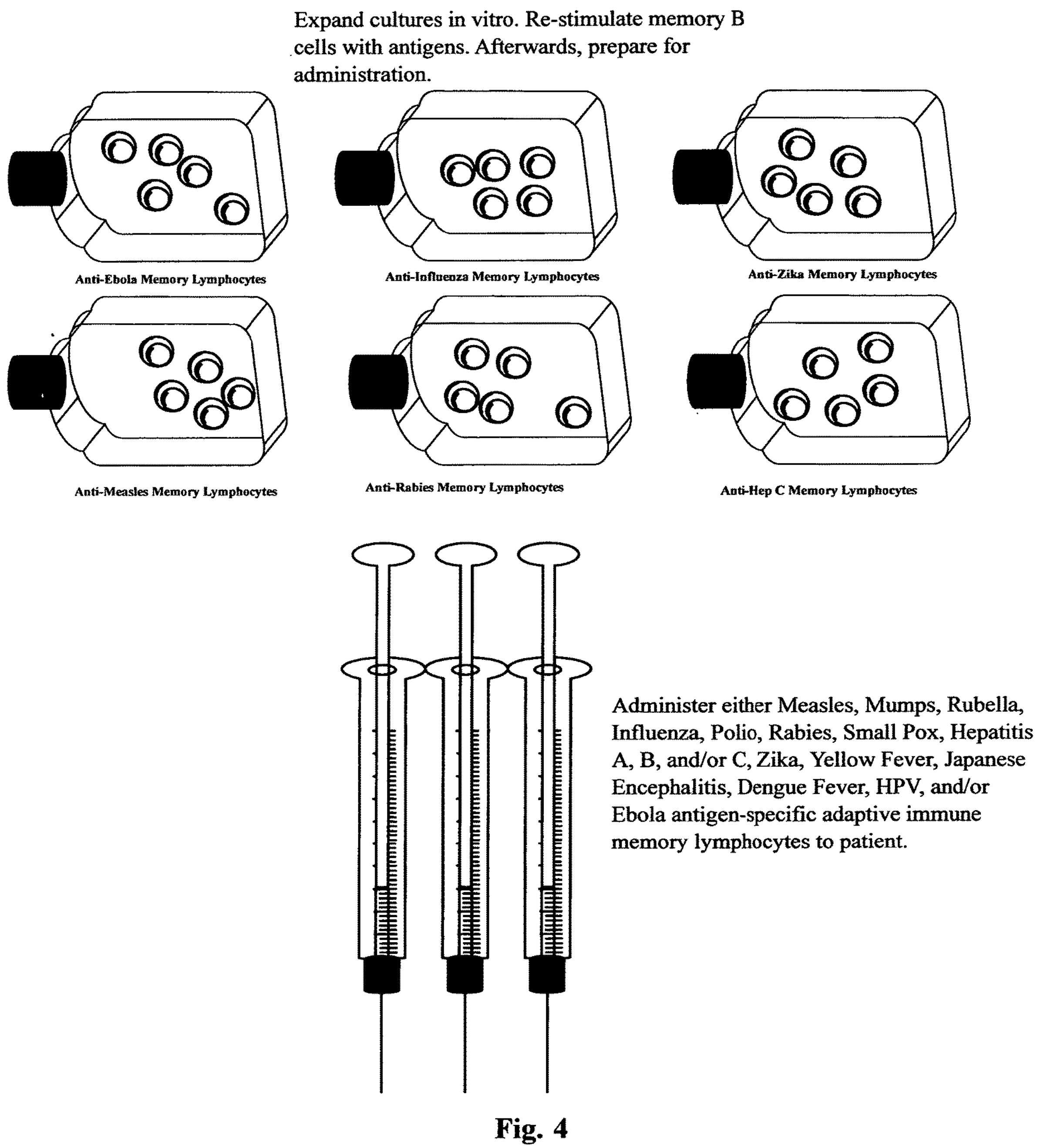

In certain embodiments, Influenza antigen-specific memory B lymphocytes which were created in vitro undergo genetic modifications wherein genes for broadly neutralizing antibodies are knocked in its genome as shown in FIG. 4. For example, a sample of Influenza antigen-specific memory B lymphocytes which have an affinity against Influenza hemagglutinin have genes for broadly neutralizing antibodies such as 5J8 given in SEQ. ID NO. 1 and 2 knocked into its genome.

In embodiments, memory lymphocytes are administered in a solution derived from a patients blood plasma. As mentioned earlier, anti-vaccinators suspects that components associated in the solution of traditional vaccines contain chemicals that are detrimental to the health of a subject. In one embodiment, blood plasma is obtained prior to administration, and used for the suspension and solution of memory lymphocytes. In certain embodiments, blood plasma is derived from a donor which can be used for the solution of said lymphocytes. After blood plasma collection, place antigen-specific memory lymphocytes in said plasma and administer to patient.

Operation

Patient Examination

Patients would undergo a physical examine to determine the overall health of the patient. See, for example, meddean.luc.edu/lumen/meded/ipm/Ipm2BSEBSE_laminated %20card.pdf, for details on physical exam procedure protocols. Said patient height, weight, age, sex, gender, race, current medication, and medical history should be noted. For example, a patient's weight will play a role in the amount of memory lymphocytes which can be administered, or for example, said patient age must be at an age when the immune system is fully functional. STIs (such as HIV infection), sepsis, leukemia, or cancers that are currently being treated with radiation can halt the progression of vaccine procedures, and must be noted in the exam. If said patient is HIV positive then vaccine consideration would be halted and treatment will be recommended. In addition, said patient must be informed of genetic modification procedures to memory lymphocytes created in vitro.

Blood Extraction

Many methods of collecting blood from a subject are known to those in the skill of the art. See, for example, who.int/injection_safety/phleb_final_screen_ready.pdf for detailed information on phlebotomy procedures and safety protocols for the collection of whole blood. In preferred embodiments, whole blood is collected using a 16G needle in a 450-500 ml bag without filtration. The bag may contain chemicals such as sodium citrate, phosphate, and dextrose to prevent clotting and to provide nourishment during storage and transport. Additional chemicals can be added as needed such as adenine. Blood products can be shipped from a clinical site to a vaccine manufacturing procedure. Motion can be the motion associated with shipping. In another embodiment, cells can be gently rocked or rotated during incubation.

In yet another embodiment, whole blood can be collect using the venipuncture method with preferably a 21G butterfly needle, preferably in 10 ml tubes. Venipuncture can be applied when extra blood is needed in vaccine production or if certain blood cells are to be collected at a later date such as naive B lymphocytes or naive CD8 T lymphocytes.

Cell Purification

Methods of isolating PBMCs from peripheral blood are known to those of skill in the art. Isolation can be done through density centrifugation and/or magnetic cell isolation, or through FACS (fluorescence-activated cell sorting). In preferred embodiments, magnetic cell isolation kits are used to collect PBMCs directly from whole blood. See, for example, www.stemcell.com/products/brands/rosettesep.html for products and directions on isolation procedures. PBMCs that are to be isolated are monocytes, naive T lymphocytes (CD4s and CD8s) and naive B lymphocytes. Monocytes can be cultured in eight welled suspension flask or in 100 ml flask containing mammalian cell culture medium and penicillin if needed. Naive CD4 T lymphocytes, Naive CD8 T lymphocytes, and Naive B lymphocytes, can be cultured in 300 ml suspension flask containing RPMI 1640 medium supplemented with 10% fetal calf serum (FCS), 1% sodium-pyruvate, 1% L-glutamine, 1% Penicillin/Streptomycin (10,000 U/ml/10,000 mg/ml), and 2% Hepes (1M, pH7.3) and optional leukemia inhibitor factors. Naive T lymphocytes are to be cultured in 3 .mu.g/ml phytohemaglutinine for 3 days and expanded with 5-20 U/ml recombinant interleukin-2 (rIL-2) for 5-6 days or until a minimum 0.5 million cells/ml in a minimum volume of 300 ml with the flask cap loosened to allow diffusion of oxygen. Naive B lymphocytes are to be cultured in 5-20 U/ml recombinant interleukin-2 (rIL-2) in the presence of recombinant CD40 ligand (rCD40L) for 5-6 days or until a minimum of 0.5 million cells/ml in a minimum volume of 300 ml with the flask cap loosened to allow diffusion of oxygen. Examine each flask under a microscope and check for signs of abnormalities. Place samples in a humidified incubator set at 37 degrees Celsius and 5% CO.sub 2. Monitor cultures daily and change medium when needed; preferably, every 2-3 days.

Monocyte Differentiation

Methods of monocyte differentiation are known to those in the skill of the art. Enriched monocytes are differentiated into dendritic cells by culture in the presence of GM-CSF and IL-4 (see, e.g., U.S. Pat. No. 7,030,228). Commercial kits can be used for differentiation and expansion of macrophages and dendritic cells from monocytes. In one embodiment, monocytes are differentiated into dendritic cells by culture in medium comprising a composition that induces differentiation of monocytes into dendritic cells. Suitable media for the culture of monocytes, immature and mature dendritic cells includes, but is not limited to, AIM-V, X-VIVO-15, RPMI, DMEM, and the like. Compositions that induce the differentiation of monocytes into dendritic cells are known in the art, and includes but are not limited to, GM-CSF plus IL-4; GM-CSF plus IL-13. Briefly, enriched monocytes, preferably at a concentration of 1.times.10.sup.6 cells/ml are cultured in AIM-V medium, X-VIVO 15 medium, or other suitable medium in the presence 800 U/ml GM-CSF and 500 U/ml IL-4 for approximately 5-7 days, preferably 6 days in a humidified incubator set at 37.degree. C., 5% CO.sub.2 to allow the differentiation of monocytes into immature dendritic cells. Cytokine concentrations can be varied. As the monocytes differentiate into dendritic cells, they progressively lose expression of CD14 and acquire CD80 expression consistent with the phenotype of dendritic cells in the immature state.

In an alternative embodiment, monocytes are differentiated into macrophages comprising a composition that induces differentiation of monocytes into macrophages. Suitable media for the culture of monocytes includes, but is not limited to, AIM-V, X-VIVO-15, RPMI, DMEM, and the like. Composition that induces the differentiation of monocytes into macrophages are known to those in the skill of the art, and include, but are not limited to, M-CSF plus IL-4. Briefly, enriched monocytes, preferably at a concentration of 1.times.10.sup.6 cells/ml are cultured in AIM V medium, X-VIVO 15 medium, or other suitable medium in the presence 800 U/ml M-CSF and 500 U/ml IL-4 for approximately 4-7 days, preferably 6 days in a humidified incubator set at 37.degree. C., 5% CO.sub.2 to allow the differentiation of monocytes macrophages. Cytokine concentration can be varied.

Antigen Loading

Methods of loading APCs with antigens/pathogens are known to those of skill in the art. After four-five days examine cultures and replace medium if needed. Once the vitality of the cultures have been established, introduce viral pathogens to professional antigen presenting cells (Dendritic Cells, Macrophages, and B lymphocytes). The APCs will then process said pathogen and present protein antigens on its cell surface in association with MHC molecules. Mix cells and medium in which they are suspended in with a pipet. Return cultures to incubator. Incubate cells for 12-24 hours at 37 degrees celsius. Pathogens can be pulsed with any professional antigen presenting cells (Dendritic cells, Macrophages, and/or B lymphocytes); however, the preferred antigen presenting cells (APCs) are immature or mature dendritic cells. The pathogen will then be processed and pathogen protein antigens presented on the major histocompatibility complexes I or II. Examples of dendritic cell and macrophage viral pathogens include, but are not limited to, either live (attenuated) strains of Measles, Mumps, Rubella, Zika, Yellow Fever, Small Pox, Varicella Zoster, or inactivated viruses (killed whole virus) such as Polio (Salk), Rabies, Hepatitis A, Hepatitis B, Hepatitis C, HPV (Human Papilloma Virus), Influenza, Japanese Encephalitis, etc. Examples of dendritic cell protein antigens, nucleic acid encoding protein antigens or viral particles includes, but are not limited to, Ebola, whooping cough, tuberculosis, etc., see, for example, 20120251502 for Ebola virus particles. Dendritic cells may be loaded with one or more pathogenic strains of a particular pathogen as immature dendritic cells, mature dendritic cells, or during differentiation from immature to mature dendritic cells. For example, dendritic cells or macrophages can be loaded with different strains of Influenza or different strains of Hepatitis C. Dendritic cells are capable of ingesting antigens, such as proteins, peptides, nucleic acids, viruses, bacteria and the like. Pathogen loading can be performed simply by contacting the dendritic cell (pulsed) with the pathogen.

Antigen Presentation and Cellular Expansion

Methods for performing antigen presentation are known to those in the skill of the art. Professional APCs which have undergone phagocytosis and display's loaded MEW II molecules with pathogenic antigens are to be diluted with naive lymphocytes. In one embodiment, loaded dendritic cells are diluted in flasks containing naive T lymphocytes (CD4 and CD8) preferably on a 1:1 ratio. In another embodiment, dendritic cells are diluted in flasks containing naive B and T lymphocytes, preferably on a 1:1 ratio. In yet an alternative embodiment, loaded B lymphocytes act as the APC to present to naive CD4 T lymphocytes. Cytokines such as rIL 10 or rIL 15 can be added to culture medium to promote differentiation of naive lymphocytes to memory lymphocytes after stimulation. Incubate cultures for seven through fourteen days preferably in a system that promote cellular expansion such as Xuri Cell Expansion System W25, see, for example promo.gelifesciences.com/GL/XURI/ expansion.html#.WF5WGqOZM0o for detail description and directions for said device. Monitor cultures daily and check for signs of cell growth, viability, and cytokine production such as IL2.

Collecting Memory Cells

Collect and isolate memory T and B lymphocytes from cultures or from cellular expansion systems. A variety of methods are available to collect and isolate T and B lymphocytes from culture by those skilled in the art. Centrifuge sample for 5 minutes at 200G. Collect supernatant and store in tubes, afterward collect cell pellet and place memory lymphocytes into a prepared flask according to their antigenic target and affinity against their particular pathogenic species. In one embodiment, FACs is used to further isolate lymphocytes according to their species and antigenic targets. Examine cultures under a microscope and check for signs of abnormalities. Afterward, place cultures in an incubator set at 37 degrees celsius.

Antibody Testing

A variety of techniques are available in the art of testing antibody affinity and neutralizing capabilities against pathogenic antigens and are known to those of skill in the art. Techniques include but are not limited to Enzyme Immunoassays such as Elisa (Enzyme-linked Immunosorbent Assay) or Western Blotting. In preferred embodiments, antibody affinity against said antigens is tested through western blotting after a gel electrophoresis of the sample. See, for example, www.ncbi.nlm.nih.gov/pmc/articles/PMC3456489/ for a detailed description of western blotting procedures. Test supernatant which contained B lymphocytes from prior cellular expansion for neutralizing antibodies, and determine said antibody affinity for their targeted antigen.

Memory B Lymphocyte Training and Genetic Modification

Memory B lymphocytes can be re-stimulated against their targeted pathogen in vitro, in the presence of armed helper T lymphocytes and/or recombinant CD40 ligand. For example, Influenza antigen-specific memory B lymphocytes are re-stimulated with either a similar or different strain of Influenza pathogens in the presence of armed helper T lymphocytes, and/or recombinant CD40 ligand or Hepatitis C antigen-specific memory B lymphocytes are re-stimulated with similar or different strains of Hepatitis C pathogens in the presence of armed helper T lymphocytes and/or recombinant CD40 ligand. In another embodiment, genes encoding anti-influenza broadly neutralizing antibodies are knocked-in to a sample of Influenza antigen-specific memory B lymphocytes genes which contain variable region coding sequences for light and/or heavy chains using commercial kits such as CRISPR see, for example, http://www.origene.com/search ProductList.aspxkeyword=variable+region&go.x=0&go.y=0. Methods for knocking in genes are known to those of skill in the art, see, for example, U.S. Pat. No. 9,273,118. Examples of genes encoding Influenza broadly neutralizing antibodies are given in SEQ ID NO 1-8. Samples of memory B lymphocytes educated against hemagglutinin are to be isolated in new flasks containing fresh culture medium as discussed earlier. After isolation, knock-in genes for broadly neutralizing antibodies, for example, 5J8 etc., using CRISPR/CAS, or other methods known to those of skill in the art. Knock-out genes in memory B lymphocytes immunoglobulin lambda or kappa locus (IGLV) variable region located on chromosome 22, and knock-in genes for variable light chains encoding light chains for Influenza broadly neutralizing antibodies. In addition knock-out genes in memory B-lymphocyte immunoglobulin heavy chain (IGHV) variable region located on chromosome 14, and knock in genes for variable region heavy chain for broadly neutralizing antibodies. Genes for broadly neutralizing antibodies are provided in the form of cDNA, see for example, origene.com/orf utm_source=Bing&utm_medium=cpc&utm=cDNA %2Bclone&&utm_content=cDNA %2Bclones&utm_campaign=Top %2BKeywords for products and details on cDNA.

Once genetic modifications have been performed, restimulate said memory lymphocytes with antigens in the presence of helper T cells and/or recombinant CD40 ligand. Cytokines such as IL2 can be added to culture medium to stimulate proliferation. After seven-twenty days, isolate memory lymphocytes using FACS and check for BCRs indicating a similarity with the antibodies of interest. In addition, check culture medium using techniques discussed earlier for neutralizing antibodies affinity against targeted antigen. Re-stimulate memory B lymphocytes with antigens if necessary. Once desired antibodies are obtained, prepare memory B lymphocytes for administration to subject.

Vaccine Solution

The vaccine solution will consist primarily of the patients blood plasma. Blood plasma will be collected from the patient prior to administration. Blood plasma can be obtained using devices such as Alyx see, for example, fenwalinc.com/Pages/Alyx.aspx for products and directions on said product. Blood plasma can be kept frozen until needed. If blood plasma was kept frozen, heat said plasma to 37 degrees Celsius before introducing memory lymphocytes. Memory lymphocytes can be suspended in blood plasma just prior to administration or memory lymphocytes can be suspended in plasma during storage.

Administration

Administration can be by methods known in the art to successfully deliver lymphocytes into contact with a subject's blood or near key organs/secondary organs of the lymphatic system such as the lymph nodes. Chemokine's can be added to the solution to encourage migration to the key structures of the lymphatic system such as the lymph nodes. Memory cells can be stored in a blood bank until administration. Cells are administered in any suitable manner, often with pharmaceutically acceptable carriers. Suitable methods of administering cells in context of the present invention to a subject are available, and although more than one route can be used to administer a particular cell composition. Routes of administration to said patient consist of intra lymphatic, intravenous. In embodiments, antigen-specific central memory CD4 and CD8 T cells, effector memory CD4 and CD8 T cells, and memory B cells can be administered intravenously and/or intralymphaticly. In vivo, said lymphocytes migrate to secondary lymphoid organs, bone marrow, spleen, and/or circulates in the peripheral blood, lymphatic fluid, and interstitial fluid. In one regard in respect to the invention, antigen-specific memory B lymphocytes which were stimulated with antigens in vitro and maintained loaded MHC complexes when administered, may interact with either administered antigen-specific memory T cells or antigen-specific naive T cells in vivo which may cause said B cells to activate and differentiate into plasma cells, memory plasma cells, and more antigen specific memory B cells. In another regard in respect to the invention, memory plasma cells which develop in vivo from loaded memory B cells, may migrate to a permanent site of residency such as the bone marrow or spleen and illicit their effector functions such as antibody secretion.

Advantage (a) It provides a method of vaccination wherein the components of said vaccine consist primarily of the patients immune memory cells blood plasma.

(b) It provides a method of vaccination for patients who would normally experience complications from the traditional vaccine approach such as pregnant women, those who are allergic to the traditional vaccine, etc.

(c) It provides a method of vaccination that does not elicits an immune response upon inoculation which anti-vaccinators often mistaken with infection from the pathogen.

(d) It provides a method of vaccination which does not inoculate whole killed or attenuated pathogens into a patient which is opposed by anti-vaccinators.

(e) It provides a method of vaccination which does not include the use of thimerosal, aluminum, or formaldehyde which is shunned by anti-vaccinators.

Conclusion

Accordingly, the reader will see that the vaccine closures of the various embodiments can be used to generate antigen-specific Immunological memory in a subject that rejects classical vaccination.

---

What is claimed is:

1. A method for generating immunological memory against influenza virus in a subject, comprising:

(a) purifying naïve T and B lymphocytes from the subject, wherein the subject is an autologous donor, (b) culturing and pulsing said naïve T and B lymphocytes with influenza virus antigens in the presence of antigen-presenting cells loaded with influenza virus antigens and cytokines, thereby generating anti-influenza antigen-specific memory T and B lymphocytes, (c) genetically modifying said anti-influenza antigen-specific memory B lymphocytes to incorporate exogenous nucleic acid sequences encoding an anti-influenza broadly neutralizing antibody binding influenza antigen, and (d) administering said anti-influenza antigen-specific memory T lymphocytes generated in step (b) and anti-influenza antigen-specific memory B lymphocytes, generated in step (c) to said subject.

2. The method of claim 1, wherein the anti-influenza antigen-specific immune memory T lymphocytes are CD4 T lymphocytes, and/or CD8 T lymphocytes.

3. The method of claim 1, wherein genetically modifying said anti-influenza antigen-specific memory B lymphocytes comprises CRISPR (Clustered Regularly interspaced Short Palindromic Repeats) Cas 9 incorporation of exogenous nucleic acid sequences encoding an anti-influenza broadly neutralizing antibody comprising at least two of SEQ ID NO: 1-8.

* * * * *